United States Patent
Amino et al.

(10) Patent No.: US 10,129,474 B2
(45) Date of Patent: Nov. 13, 2018

(54) OBSERVATION APPARATUS, MEASUREMENT SYSTEM AND OBSERVATION METHOD

(71) Applicant: OLYMPUS CORPORATION, Hachioji-shi, Tokyo (JP)

(72) Inventors: Hiroki Amino, Hino (JP); Katsuhisa Kawaguchi, Atsugi (JP); Koji Aota, Machida (JP); Osamu Nonaka, Sagamihara (JP)

(73) Assignee: Olympus Corporation, Tokyo (JP)

( * ) Notice: Subject to any disclaimer, the term of this patent is extended or adjusted under 35 U.S.C. 154(b) by 88 days.

(21) Appl. No.: 15/435,113

(22) Filed: Feb. 16, 2017

(65) Prior Publication Data
US 2017/0257569 A1    Sep. 7, 2017

(30) Foreign Application Priority Data

Mar. 3, 2016    (JP) .................. 2016-041434

(51) Int. Cl.
| | |
|---|---|
| H04N 5/232 | (2006.01) |
| G06K 9/32 | (2006.01) |
| H04N 5/225 | (2006.01) |
| G01N 33/483 | (2006.01) |
| G01N 33/487 | (2006.01) |
| G02B 21/00 | (2006.01) |
| H04N 5/349 | (2011.01) |

(52) U.S. Cl.
CPC ..... *H04N 5/23245* (2013.01); *G01N 33/4833* (2013.01); *G01N 33/48735* (2013.01); *G02B 21/0016* (2013.01); *G06K 9/3233* (2013.01); *H04N 5/2258* (2013.01); *H04N 5/23203* (2013.01); *H04N 5/23232* (2013.01); *H04N 5/23296* (2013.01); *G06K 2209/05* (2013.01); *H04N 5/23212* (2013.01); *H04N 5/349* (2013.01)

(58) Field of Classification Search
CPC ............. G02B 21/0016; G06K 9/3233; G06K 2209/05; G01N 33/4833; G01N 33/48735; H04N 5/23245; H04N 5/2258; H04N 5/23203; H04N 5/23232; H04N 5/23296; H04N 5/23212; H04N 5/349
See application file for complete search history.

(56) References Cited

FOREIGN PATENT DOCUMENTS

JP    2005-295818    10/2005

*Primary Examiner* — Huy T Nguyen
(74) *Attorney, Agent, or Firm* — John C. Pokotylo; Pokotylo Patent Services

(57) ABSTRACT

An observation apparatus includes an imaging unit, a driving mechanism and a control unit. The imaging unit takes images of a target object. The driving mechanism moves the imaging unit to change an observation position of the target object. The control unit controls the driving mechanism and the imaging unit while switching between a first mode in which the imaging unit takes images while simultaneously being moved at a high speed by the driving mechanism, and a second mode in which the imaging unit takes images having a higher resolution than the images taken in the first mode while simultaneously being moved at a speed lower than that of the first mode.

16 Claims, 13 Drawing Sheets

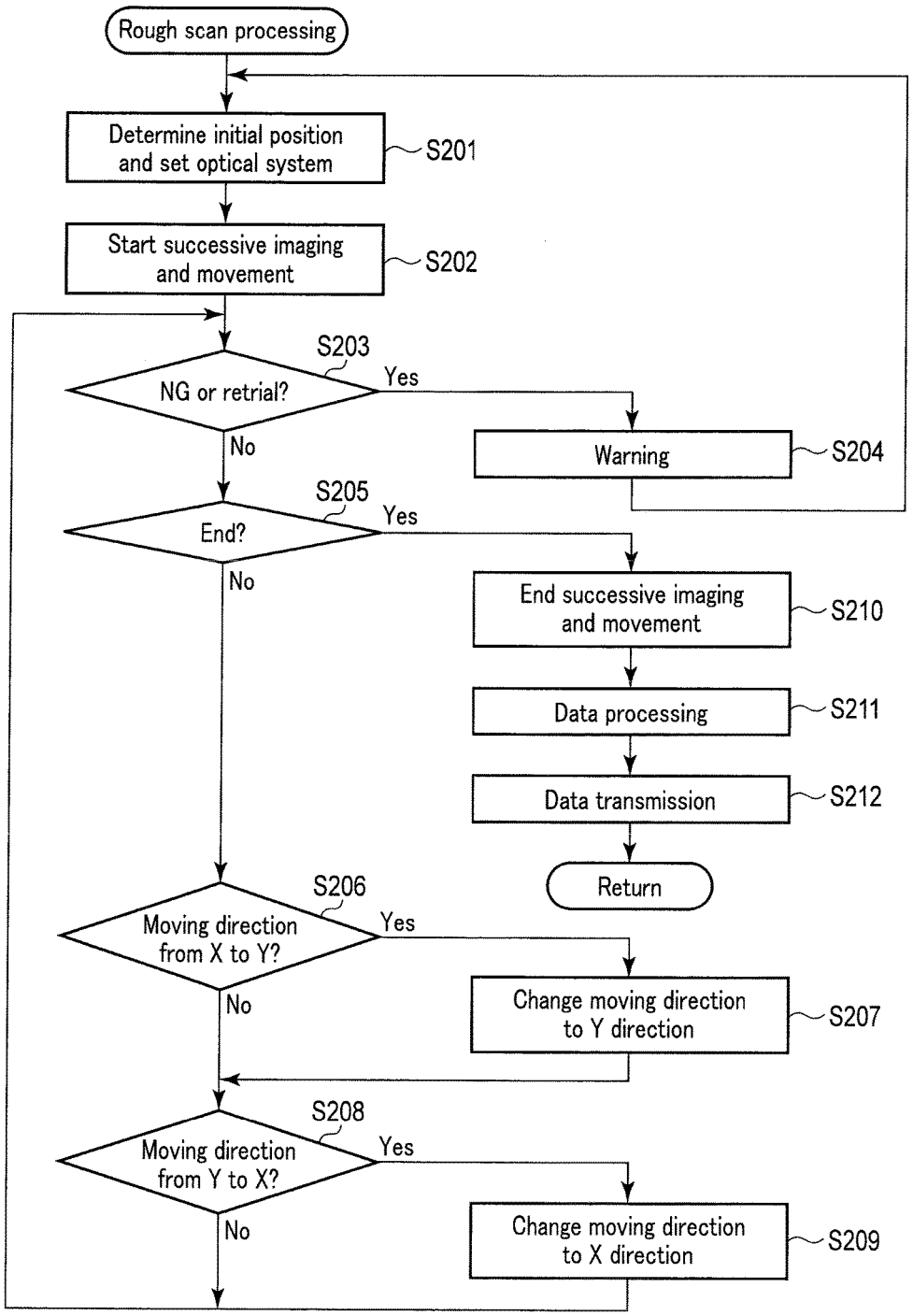
F I G. 8

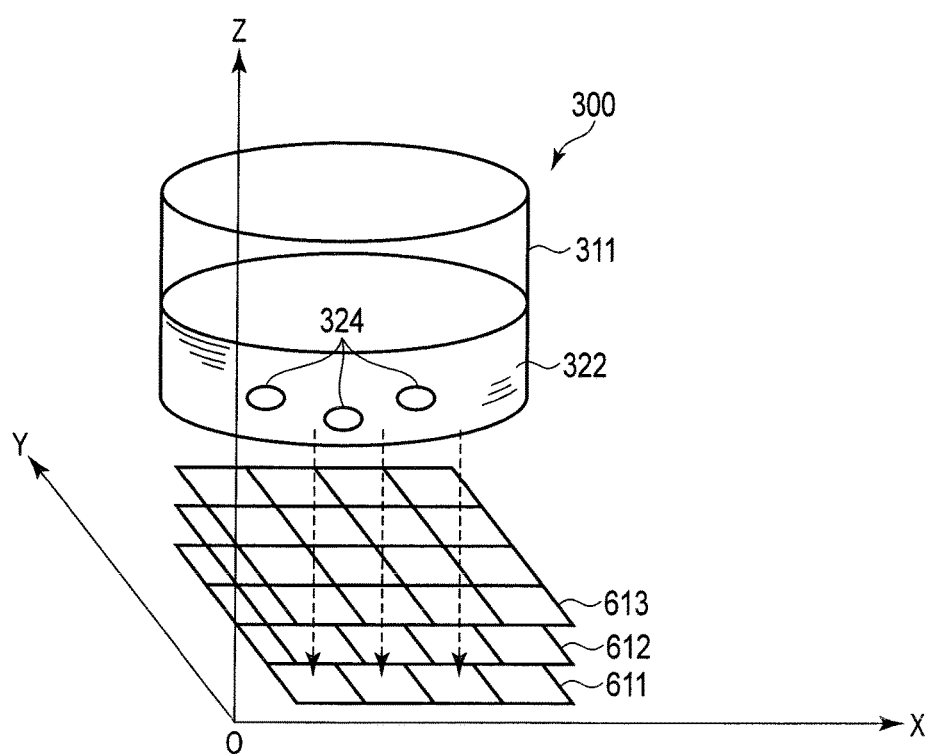
F I G. 10

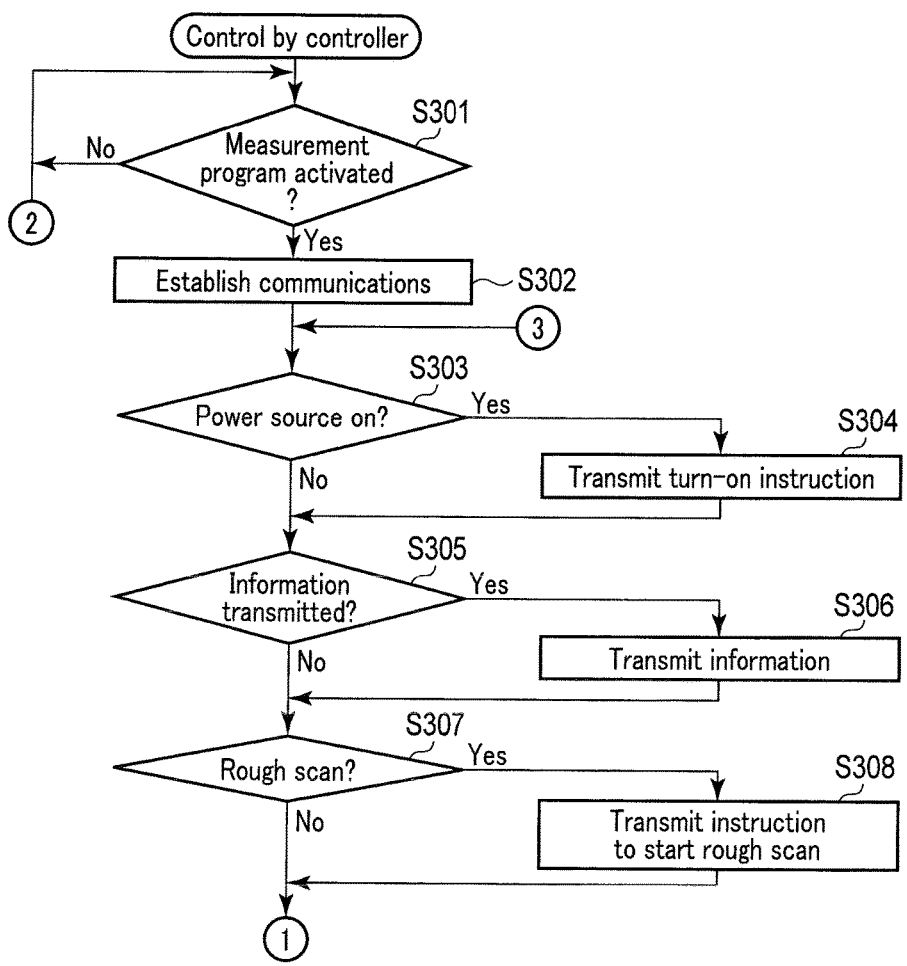
F I G. 13A

OBSERVATION APPARATUS, MEASUREMENT SYSTEM AND OBSERVATION METHOD

CROSS-REFERENCE TO RELATED APPLICATIONS

This application is based upon and claims the benefit of priority from prior Japanese Patent Application No. 2016-041434, filed Mar. 3, 2016, the entire contents of which are incorporated herein by reference.

BACKGROUND OF THE INVENTION

1. Field of the Invention

The present invention relates to an observation apparatus, a measurement system and an observation method 2. Description of the Related Art In general, an apparatus wherein a culture vessel is statically placed in an incubator and images of cultured cells or the like in the culture vessel are taken, is known in the art. For example, Jpn. Pat. Appln. KOKAI Publication No. 2005-295818 discloses a technique related to an apparatus which takes a number of images while moving a camera (imaging unit) inside an incubator so as to take images of cells existing in a wide range of a culture vessel.

BRIEF SUMMARY OF THE INVENTION

According to one aspect of the invention, an observation apparatus includes an imaging unit which takes images of a target object; a driving mechanism which moves the imaging unit to change an observation position of the target object; and a control unit which controls the driving mechanism and the imaging unit while switching between (i) a first mode in which the imaging unit takes images while simultaneously being moved at a high speed by the driving mechanism, and (ii) a second mode in which the imaging unit takes images having a higher resolution than that of the images taken in the first mode while simultaneously being moved at a speed lower than that of the first mode.

According to one aspect of the present invention, a measurement system includes the above-mentioned observation apparatus which further includes a communication device; and a controller which communicates with the observation apparatus via the communication device and controls the observation apparatus.

According to one aspect of the invention, an observation method includes causing an imaging unit to image a target object; moving the imaging unit to change an observation position of the target object; and controlling the imaging unit while switching between (i) a first mode in which the imaging unit takes successive images while simultaneously being moved at a high speed by the driving mechanism, and (ii) a second mode in which the imaging unit takes successive images having a high resolution than that of the images taken in the first mode while simultaneously being moved at a speed lower than that of the first mode.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 8 is a flowchart illustrating an example of rough scan processing according to one embodiment.

FIG. 10 is an explanatory diagram illustrating image acquisition performed by an observation apparatus according to one embodiment.

FIG. 13A is a flowchart illustrating an example of processing performed by a controller according to one embodiment.

DETAILED DESCRIPTION OF THE INVENTION

Embodiments of the present invention will now be described with reference to the accompanying drawings. The measurement system of the present embodiment is a system which takes images of a cell, a cell group and a tissue which are being cultured, and which makes a record of the numbers of cells or cell groups and the morphology thereof.

<Configuration of Measurement System>

Figure 1:
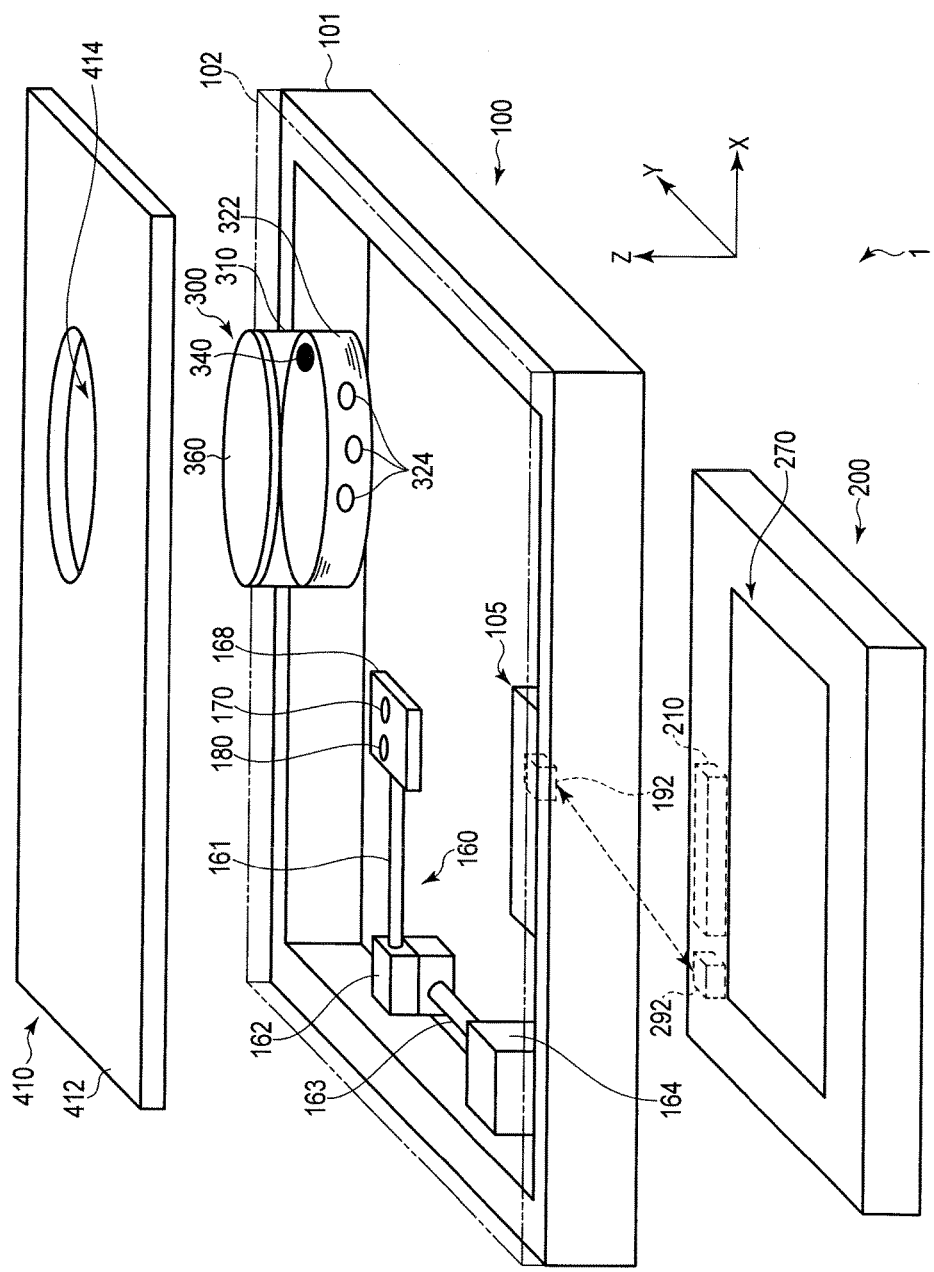
FIG. 1 schematically illustrates an exemplary configuration of a measurement system according to one embodiment.
Figure 2:
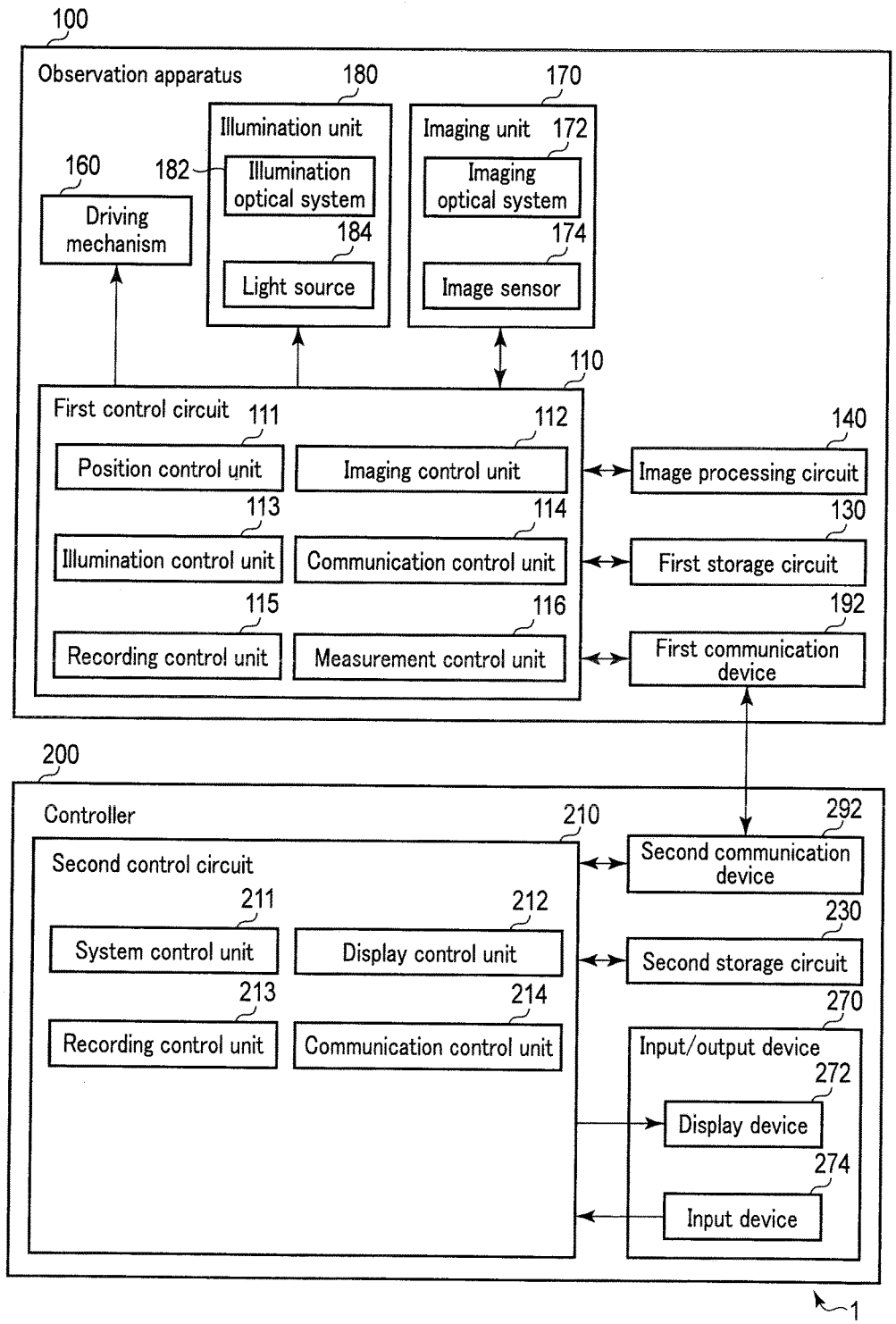
FIG. 2 is a block diagram schematically illustrating an exemplary configuration of the measurement system according to the embodiment.

FIG. 1 is a schematic diagram schematically illustrating how the measurement system 1 looks like. FIG. 2 is a block diagram illustrating an exemplary configuration of the measurement system 1. The measurement system 1 comprises an observation apparatus 100 and a controller 200. As shown in FIG. 1, the observation apparatus 100 is shaped substantially like a plate. The observation apparatus 100 is provided, for example, inside an incubator, and a sample 300 to be observed is arranged on top of the observation apparatus 100. For the sake of explanation, an x-axis and a y-axis perpendicular to each other are defined in a plane parallel to the surface on which the sample 300 is arranged, and a z-axis is defined as an axis perpendicular to both the x-axis and the y-axis. A transparent plate 102 is placed as a top plate of the observation apparatus 100, and an imaging unit 170 is provided inside the casing 101 of the observation apparatus 100. The observation apparatus 100 takes an image of the sample 300, with the transparent plate 102 interposed, and the image of the sample 300 is acquired thereby. On the other hand, the controller 200 is provided on the outside of the incubator. The observation apparatus 100 and the controller 200 communicate with each other. The controller 200 controls the observation apparatus 100.

(Sample)

An example of the sample 300 to be observed by the measurement system 1 will be described. A culture medium 322 is in the vessel 310, and cells 324 are cultured in the culture medium 322. The vessel 310 is, for example, a petri dish, a culture flask, a multiwell plate, or the like. The vessel 310 is a culture vessel for culturing a living specimen, for example. The vessel 310 is not limited to any specific shape or size. The culture medium 322 may be either a liquid medium or a solid medium. The cells 324 to be measured may be either adhesive cells or floating cells. Alternatively, the cells 324 may be spheroids or tissues. In addition, the cells 324 may be derived from any living substance or may be bacteria or the like. As described above, the sample 300 includes a living sample which is either the living substance itself or is derived from the living substance.

Where the culture medium 322 is a liquid medium, a buoy 340 may float on the medium 322. The buoy 340 serves as a mark for confirming the upper level of the medium 322. A reflecting plate 360 is on top of the vessel 310. The reflecting plate 360 reflects illumination light, described later.

(Observation Apparatus)

As shown in FIG. 1, a transparent plate 102 made, for example, of glass is on top of the casing 101 of the observation apparatus 100. The sample 300 is statically placed on this transparent plate 102. Although FIG. 1 shows that the top plate of the casing 101 is entirely transparent, the observation apparatus 100 may be designed such that part of the top plate of the casing 101 is a transparent plate, and the remaining part of the top plate is an opaque.

The transparent plate 102 may be overlaid with a fixing frame 410 to determine the position where the sample 300 is placed on the transparent plate 102 and fix the sample 300. The fixing frame 410 may be designed such that it is arranged at a specific position with respect to the transparent plate 102. For example, the fixing frame 410 may have the same size as the transparent plate 102. The fixing frame 410 includes a fixing plate 412 and a hole 414 formed in the fixing plate 412. The hole 414 has a diameter slightly larger than the outer diameter of the vessel 310 of the sample 300. In the state where the fixing frame 410 is placed on the transparent plate 102, the vessel 310 can be fixed in the hole 414. A plurality of fixing frames 410 of different types may be prepared in accordance with the types of vessels 310 of the sample 300. The fixing frame 410 may be employed; alternatively, it can be omitted.

Various structural elements of the observation apparatus 100 are provided inside the casing 101. The interior of an incubator has a temperature of 37° C. and a humidity of 95%. Since the observation apparatus 100 is used in an environment of high ambient temperature and humidity, the casing 101 is designed have an air-tight structure.

A support member 168, which is inside the casing 101, is provided with an illumination unit 180 for illuminating the sample 300. The illumination unit 180 emits illumination light in the direction toward the transparent plate 102, namely, in the direction toward the sample 300. As shown in FIG. 2, the illumination unit 180 includes an illumination optical system 182 and a light source 184. The illumination light emitted from the light source 184 is made to travel to the sample 300 by the illumination optical system 182. Although the illumination unit 180 was described as being provided for the support member 168, what is required in practice is merely that the output end of the illumination optical system 182 is arranged in the support member 168. As long as this requirement is met, the light source 184 may be arranged at any position in the observation apparatus 100.

As shown in FIG. 1, the imaging unit 170 is provided in the neighborhood of the illumination unit 180 of the support member 168. The imaging unit 170 takes an image of the region where the sample 300 is present, and thus acquires an image of the sample 300. As shown in FIG. 2, the imaging unit 170 includes an imaging optical system 172 and an image sensor 174. The imaging unit 170 generates image data based on an image which is formed on the imaging plane of the image sensor 174 by the imaging optical system 172. The imaging optical system 172 is preferably a zoom optical system capable of changing its focal distance.

Figure 3:
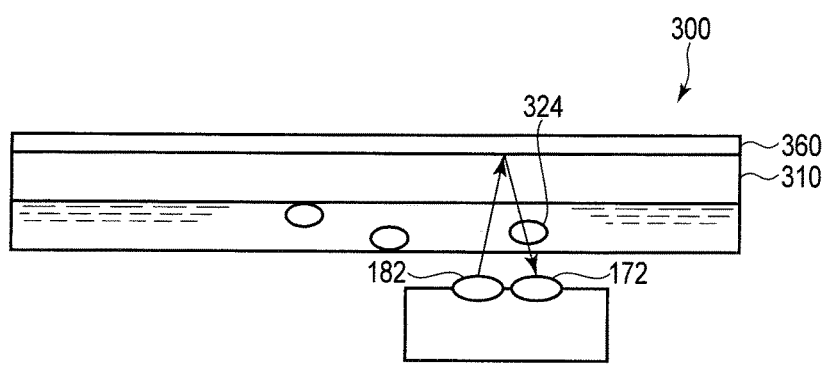
FIG. 3 is a side view showing an exemplary configuration of a support member and a sample according to one embodiment.

FIG. 3 is a schematic diagram illustrating a side view of the sample 300. As shown in FIG. 3, the illumination light output from the illumination optical system 182 of the illumination unit 180 falls on the reflecting plate 360 provided on top of the vessel 310, and is reflected by the reflecting plate 360. The reflected light illuminates the cells 324 and is incident on the imaging optical system 172 of the imaging unit 170.

Turning back to FIG. 1, a description will be continued. The support member 168 on which the imaging unit 170 and the illumination unit 180 are fixed is moved by a driving mechanism 160. The driving mechanism 160 is provided with an X feed screw 161 and an X actuator 162 for moving the support member 168 in the X-axis direction. The driving mechanism 160 is also provided with a Y feed screw 163 and a Y actuator 164 for moving the support member 168 in the Y-axis direction.

The imaging position in the Z-axis direction is changed by changing the focus position of the imaging optical system 172. In other words, the imaging optical system 172 is provided with a focus adjustment mechanism for moving a focusing lens in the optical direction. In place of the focus adjustment mechanism or in combination therewith, the driving mechanism 160 may be provided with a Z feed screw and a Z actuator for moving the support member 168 in the Z-axis direction.

A group 105 of circuits for controlling the driving mechanism 160, imaging unit 170 and illumination unit 180 are provided inside the casing 101. A first communication device 192 is provided for the circuit group 105. The first communication device 192 is, for example, a device which communicates with the controller 200 by wireless. The communications are wireless communications using, for example, Wi-Fi or Bluetooth. The observation apparatus 100 and the controller 200 may be connected by a cable, and cable communications may be performed between them.

As shown in FIG. 2, the observation apparatus 100 comprises a first control circuit 110, a first storage circuit 130 and an image processing circuit 140, in addition to the driving mechanism 160, imaging unit 170, illumination unit 180 and first communication device 192 described above. The first control circuit 110, the first storage circuit 130, the image processing circuit 140 and the first communication device 192 are arranged, for example, in the circuit group 105 described above.

The first control circuit 110 controls each of the elements of the observation apparatus 100. The first control circuit 110 functions as a position control unit 111, an imaging control unit 112, an illumination control unit 113, a communication control unit 114, a recording control unit 115 and a measurement control unit 116. The position control unit 111 controls the driving mechanism 160 to control the position of the support member 168. The imaging control unit 112 controls the imaging unit 170 to cause the imaging unit to take an image of the sample 300. The illumination control unit 113 controls the illumination unit 180. The communication control unit 114 controls the communications with the controller 200 which are performed using the first communication device 192. The recording control unit 115 controls the recording of data obtained by the observation apparatus 100. The measurement control unit 116 controls the overall measurement, including measurement times and the number of times the measurement is performed.

The first storage circuit 130 stores, for example, programs and various parameters used by the first control circuit 110. The first storage circuit 130 also stores data obtained by the observation apparatus 100.

The image processing circuit 140 performs various kinds of image processing for the image data obtained by the imaging unit 170. After the image processing by the image processing circuit 140, data is recorded in the first storage circuit 130 or transmitted to the controller 200 by way of the first communication device 192. The first control circuit 110 or the image processing circuit 140 may perform various kinds of analysis, based on the obtained image. For example, the first control circuit 110 or the image processing circuit 140 extracts an image of the cell or cell group included in the sample 300 or counts the number of cells or cell groups, based on the obtained image. The results of this analysis are recorded in the first storage circuit 130 or transmitted to the controller 200 by way of the first communication device 192.

(Controller)

The controller 200 is, for example, a personal computer (PC) or an information terminal such as a tablet type. In FIG. 1, a tablet type information terminal is depicted.

The controller 200 is provided with an input/output device 270 comprising a display device 272 (e.g., a liquid crystal display) and a input device 274 (e.g., a touch panel). The input device 274 is not limited to the touch panel but may include a switch, a dial, a keyboard, a mouse, etc.

The controller 200 is also provided with a second communication device 292. The second communication device 292 is a device which communicates with the first communication device 192. The observation apparatus 100 and the controller 200 communicate with each other through the first communication device 192 and the second communication device 292.

The controller 200 is further provided with a second control circuit 210 and a second storage circuit 230. The second control circuit 210 controls each of the elements of the controller 200. The second storage circuit 230 stores, for example, programs and various parameters used by the second control circuit 210. The second storage circuit 230 also stores data obtained by and received from the observation apparatus 100.

The second control circuit 210 functions as a system control unit 211, a display control unit 212, a recording control unit 213 and a communication control unit 214. The system control unit 211 performs various operations for controlling the measurement of the sample 300. The display control unit 212 controls the display device 272. The display control unit 212 causes the display device 272 to display the necessary information. The recording control unit 213 controls the recording of information in the second storage circuit 230. The communication control unit 214 controls the communications with the observation apparatus 100 which are performed using the second communication device 292.

Each of the first control circuit 110, image processing circuit 140 and second control circuit 210 incorporates a central processing unit (CPU), an application specific integrated circuit (ASIC), an integrated circuit such as a field programmable gate array (FPGA), or the like. Each of the first control circuit 110, image processing circuit 140 and second control circuit 210 may be constituted by a single integrated circuit or by a combination of a number of integrated circuits. The first control circuit 110 and the image processing circuit 140 may be made by a single integrated circuit. Each of the position control unit 111, imaging control unit 112, illumination control unit 113, communication control unit 114, recording control unit 115 and measurement control unit 116 of the first control circuit 110 may be constituted by a single integrated circuit or by a combination of a number of integrated circuits. Two or more of the position control unit 111, imaging control unit 112, illumination control unit 113, communication control unit 114, recording control unit 115 and measurement control unit 116 may be constituted by a single integrated circuit or the like. Likewise, each of the system control unit 211, display control unit 212, recording control unit 213 and communication control unit 214 of the second control circuit 210 may be constituted by a single integrated circuit or by a combination of a number of integrated circuits. Two or more of the system control unit 211, display control unit 212, recording control unit 213 and communication control unit 214 may be constituted by a single integrated circuit or the like. The operations of these integrated circuits are executed, for example, in accordance with programs stored in the first storage circuit 130 or second storage circuit 230, or in accordance with the programs stored in the storage regions of the integrated circuits.

<Operations of Measurement System>

Operations of the measurement system 1 will be described. The observation apparatus 100 of the measurement system 1 of the present embodiment operates in two imaging modes. To be specific, the measurement system 1 operates either in a first mode in which an overview of the sample 300 is provided by a rough scan or in a second mode in which a high-resolution image is acquired for measurement. In the first mode, the driving mechanism 160 moves the imaging unit 170 at high speed, and the imaging unit 170 quickly takes images at the sacrifice of high resolution. On the other hand, in the second mode, the driving mechanism 160 moves the imaging unit 170 at a speed lower than that of the first mode, and the imaging unit 170 takes images having a resolution higher than that in the first mode. The position control unit 111 and imaging control unit 112 of the first control circuit 110 operate the observation apparatus 100 in the first and second modes.

In order to observe, for example, a region having a square of 90 mm×90 mm, an image has to be taken 900 times in the second mode, provided that an image taken in the second mode is that of a region having a square of 3 mm×3 mm. If, in the second mode, one image can be taken per second, 900 seconds are required for imaging of the entire region. If a video is taken at 30 frames/second in the first mode, with a field of 6 mm×6 mm, the imaging is completed in 7.5 seconds. This can be accomplished by applying the technology of an image sensor of a general type digital camera, which is switchable between a video mode (wherein a video is taken at a fast frame rate, with pixels being thinned or added) and a still image mode (wherein a high-resolution image is taken). The image sensor is provided with a color filter, but the color filter may be omitted in accordance with what is to be imaged.

Figure 4:
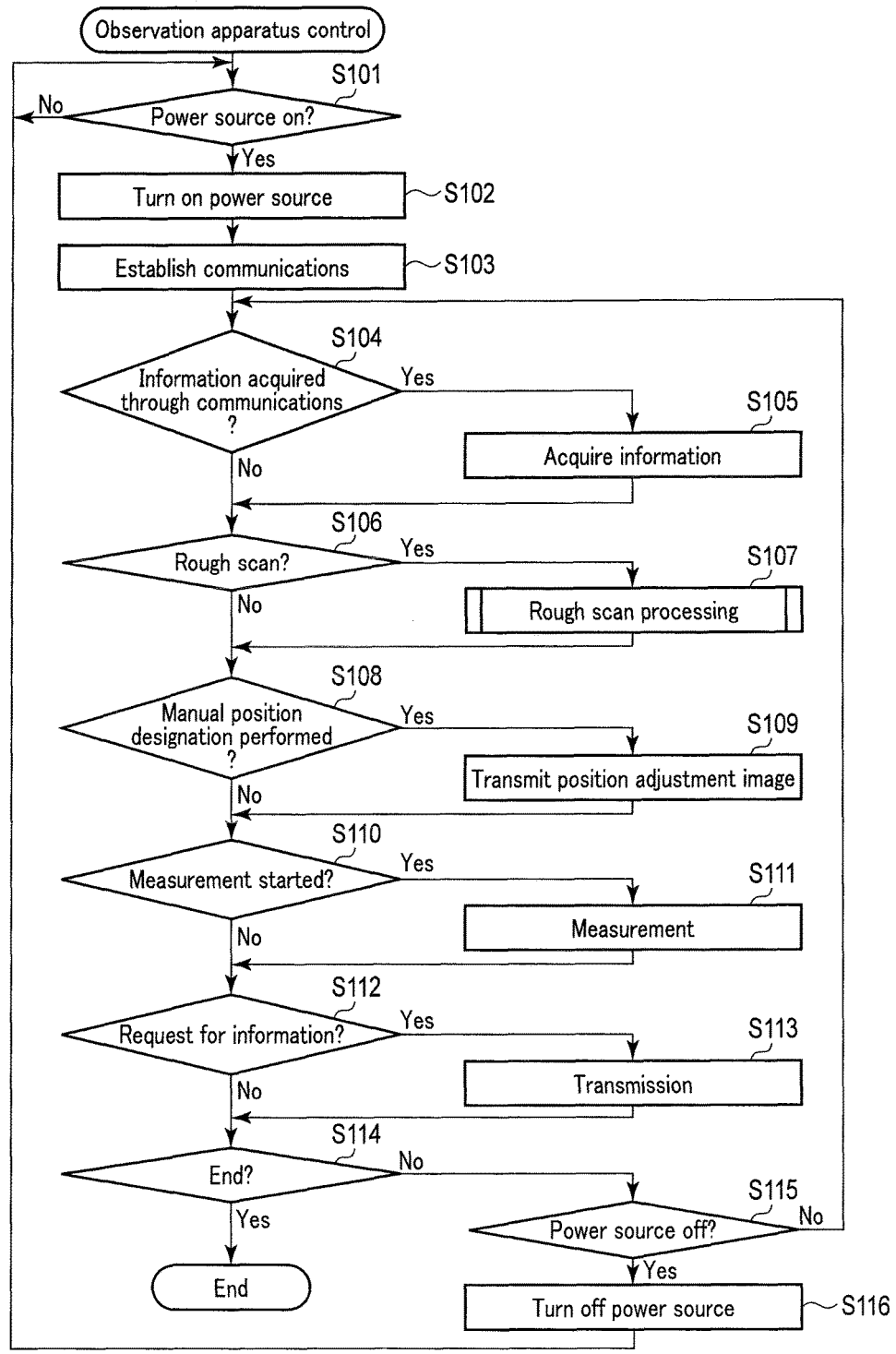
FIG. 4 is a flowchart illustrating an example of observation apparatus control processing according to one embodiment.

The operation of the observation apparatus 100 will be described with reference to the flowchart shown in FIG. 4. The flowchart shown in FIG. 4 starts when the observation apparatus 100, controller 200 and sample 300 are in place and preparations for measurement have been made.

In step S101, the first control circuit 110 determines whether or not the power source should be turned on. Where the power source is configured to be switched on at predetermined times and the time to switch on the power switch comes, the first control circuit 110 determines that the power source should be turned on. Where the observation apparatus 100 constantly communicates with the controller 200 through low-power-consumption communication means such as Bluetooth Low Energy, and when the observation apparatus 100 receives instructions to turn on the power source from the controller 200 through the communication means, it is determined that the power source should be turned on. Unless the power source is turned on, the processing stands by, repeating steps S101. If it is determined that the power source should be turned on, the processing advances to step S102.

In step S102, the first control circuit 110 turns on the power source to supply power to the respective portions of the observation apparatus 100. If the power source is turned on only when the sample 300 is measured in practice, power saving can be attained. In particular, if the power source of the observation apparatus 100 is a battery, the driving time of the observation apparatus 100 can be lengthened.

In step S103, the first control circuit 110 establishes communications with the controller 200. The communication means used in the embodiment is high-speed communication means, such as Wi-Fi.

In step S104, the first control circuit 110 determines whether or not information should be acquired from the controller 200 through the established communications. For example, when information is transmitted from the controller 200, it is determined that the information should be acquired. Unless the information is acquired, the processing advances to step S106. If the information is acquired, the processing advances to step S105.

In step S105, the first control circuit 110 acquires the information transmitted from the controller 200. The acquired information includes condition information, such as measurement conditions (including imaging conditions, imaging intervals and other parameters), a method for recording measurements, a transmission condition for the measurements, etc. Subsequently, the processing advances to step S106.

Figure 5:
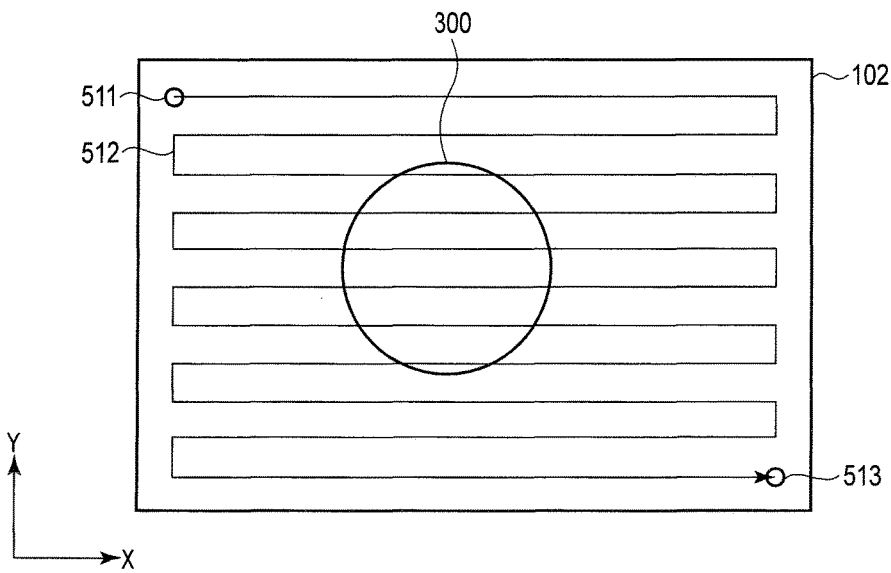
FIG. 5 is an explanatory diagram illustrating a rough scan performed by an observation apparatus according to one embodiment.
Figure 6:
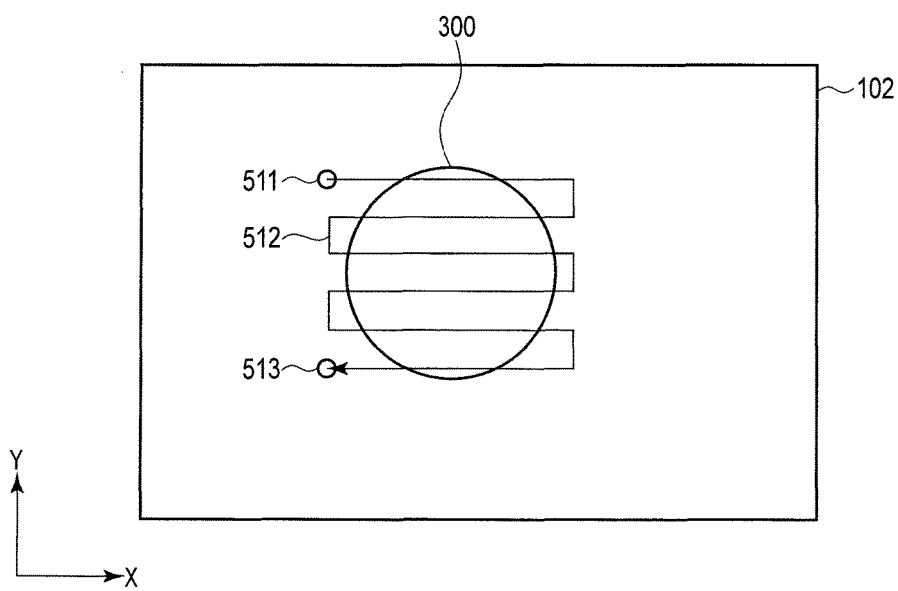
FIG. 6 is an explanatory diagram illustrating a rough scan performed by an observation apparatus according to one embodiment.

In step S106, the first control circuit 110 determines whether or not a rough scan is to be performed. A description will be given of the rough scan. The rough scan is performed prior to the imaging for measurement to provide an overview of the state of the entire sample 300. The rough scan is an imaging operation in which a short imaging time is given priority to image quality. For example, what is scanned is not just a region of interest of the sample 300 but the entire transparent plate 102, as shown in FIG. 5. For example, the imaging unit 170 is moved for imaging at high speed from the initial position 511 to the end position 513 along the route indicated by line 512. If the position of the sample 300 is known, only the range in which the sample 300 is located may be scanned, as shown in FIG. 6. In the rough scan, the imaging unit 170 takes a video, for example.

Figure 7:
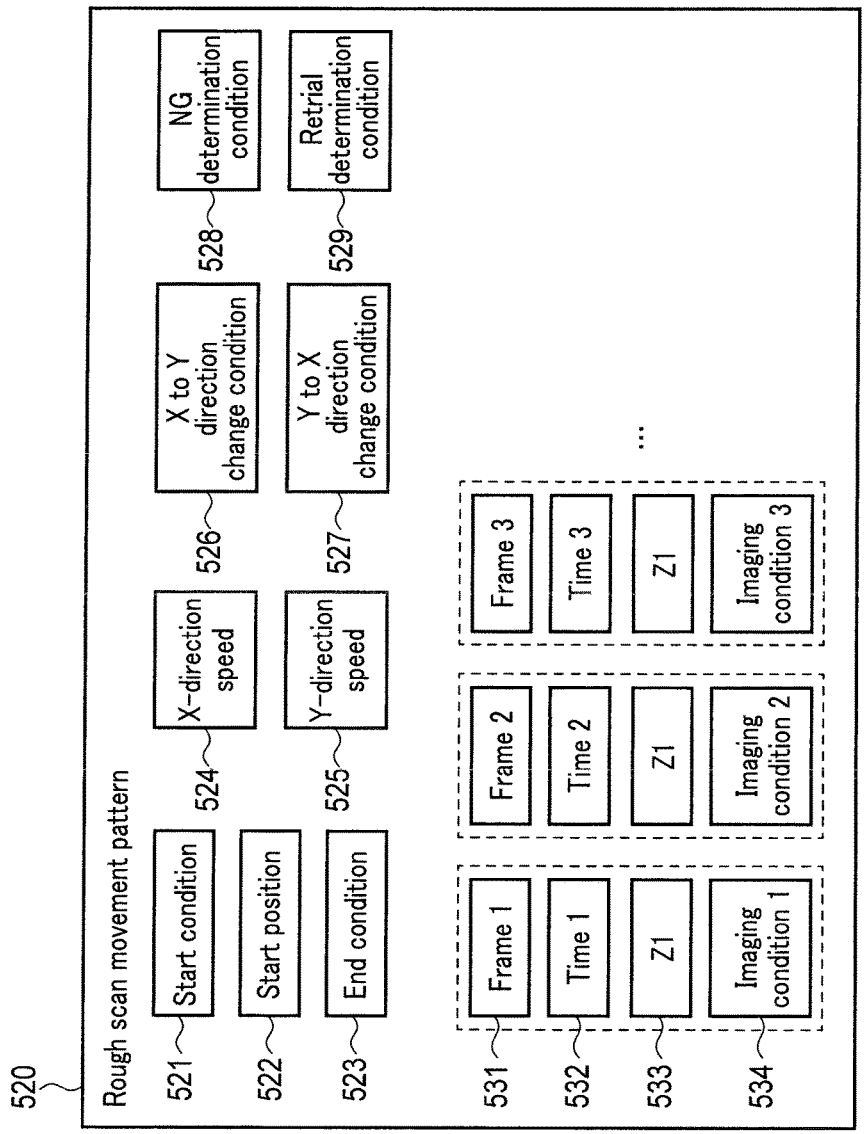
FIG. 7 is an explanatory diagram illustrating a rough scan movement pattern used by an observation apparatus according to one embodiment.

The movement pattern according to which the imaging unit 170 is moved for the rough scan is recorded in the first storage circuit 130. An example of the rough scan movement pattern 520 recorded in the first storage circuit 130 is shown in FIG. 7. The rough scan movement pattern 520 includes a start condition 521, a start position 522 and an end condition 523. The start condition 521 includes information regarding a condition under which a scan is started. The start condition 521 may include information representing whether the entire transparent plate 102 is to be scanned or whether only the range in which the sample 300 is arranged is to be scanned. The start condition 521 includes a time required for the imaging unit 170 set at the initial position to start a scan. The start position 522 includes information representing a position from which a scan is started. The start position 522 includes, for example, information representing the positions where the edges of the transparent plate 102 are located and information representing the positions where the edges of the sample 300 are located. The end condition 523 includes information regarding a condition under which a scan is ended. The end condition 523 includes, for example, information representing a position at which the scan is ended and information on the time required from the start of the scan to the end of the scan.

The rough scan movement pattern 520 further includes an X-direction speed 524, a Y-direction speed 525, an X to Y direction change condition 526 and a Y to X direction change condition 527. The X-direction speed 524 includes information representing the speed at which the imaging unit 170 is moved in the X-axis direction. The Y-direction speed 525 includes information representing the speed at which the imaging unit 170 is moved in the Y-axis direction. The X to Y direction change condition 526 includes a condition under which the moving direction of the imaging unit 170 is changed from the X-axis direction to the Y-axis direction. The X to Y direction change condition 526 includes, for example, position information representing edges of a scan region, as determined in the X-axis direction. The Y to X direction change condition 527 includes a condition under which the moving direction of the imaging unit 170 is changed from the Y-axis direction to the X-axis direction. The Y to X direction change condition 527 includes, for example, information representing a distance for which the imaging unit 170 is moved in the Y-axis direction at one time.

The rough scan movement pattern 520 includes an NG determination condition 528 and a retrial determination condition 529. The NG determination condition 528 includes a condition under which the rough scan is determined as a failure. The retrial determination condition 529 includes a condition under which the rough scan should be performed again from the start.

The rough scan movement pattern 520 may include information regarding a combination of the number of frames 531, a point of time 532, a Z coordinate 533 and an imaging condition 534.

The first storage circuit 130 may store a rough scan movement pattern 520 according to which the entire transparent plate 102 is scanned, as shown in FIG. 5. In addition to the pattern according to which the entire transparent plate 102 is scanned or in place of that pattern, the first storage circuit 130 may store a rough scan movement pattern 520 according to which part of the transparent plate 102 is scanned, as shown in FIG. 6.

The rough scan is performed using the information on the rough scan movement pattern 520. In other words, the measurement control unit 116 starts or ends the rough scan, using the information including the start condition 521, start position 522, end condition 523, NG determination condition 528, and retrial determination condition 529. The position control unit 111 moves the support member 168 bearing the imaging unit 170, using the information including the X-direction speed 524, Y-direction speed 525, X to Y direction change condition 526, and Y to X direction change condition 527. The imaging control unit 112 controls the operation of the imaging unit 170, using the information including the Z coordinate 533 and imaging condition 534. The image processing circuit 140 may analyze a video obtained by the imaging, using the information including the number of frames 531, point of time 532, X-direction speed 524, Y-direction speed 525, X to Y direction change condition 526, Y to X direction change condition 527 and Z coordinate 533.

Turning back to FIG. 4, a description will be continued. If it is determined in step S106 that the rough scan is not to be performed, the processing advances to step S108. If it is determined that the rough scan is to be performed, the processing advances to step S107. In step S106, the execution of the rough scan is determined under various conditions, for example, where the measurement by the measurement system is performed for the first time, where the user designates execution of the rough scan, where the current time is immediately before the start of repeatedly-executed measurement, and where obtained measurement results satisfy a predetermined condition.

In step S107, the first control circuit 110 performs rough scan processing. The rough scan processing will be described with reference to the flowchart shown in FIG. 8.

In step S201, the first control circuit 110 controls the driving mechanism 160 such that the imaging unit 170 moves to the initial position. In addition, the first control circuit 110 sets the imaging optical system 172 in a predetermined condition. For example, where the imaging optical system 172 is a zoom optical system, it is set in the wide angle mode, i.e., in the mode in which the focal distance is short. In addition, the first control circuit 110 decreases the opening size of the aperture of the imaging optical system 172, thereby increasing the depth of field. At the time, the first control circuit 110 may increase the intensity of the illumination light of the illumination unit 180 in accordance with the decrease in the opening size of the aperture. For example, the light emission intensity of the light source may be changed, and the filter structure of the optical path may be changed. The first control circuit 110 may increase the sensitivity of the image sensor 174. For example, the sensitivity can be increased by pixel addition in which the brightness value obtained by the pixels of the image sensor 174 is added. The gain adjustment may be made or the frame rate may be changed.

For easy understanding an overview at the sacrifice of image quality, the rough scan processing may be executed as below, in comparison with normal measurement. To be specific, in the image acquisition at the time of measurement, phase-contrast illumination is used as illumination light. In contrast, in the rough scan, focal illumination, i.e., normal illumination, may be used. The use of the focal illumination enables easy understanding of an overview even in a slightly defocused state at the time of measurement. Where the phase-contrast illumination is used, an image acquired in a defocused state may be an image including a number of overlapping images. This phenomenon is attributable to the fact that a plurality of light-emitting diodes (LED) are employed for the suppression of uneven shading. In the rough scan, only part of the LEDs may be kept lit. Where part of the LEDs are kept lit, an image enabling easy understanding of an overview can be obtained even in a slightly defocused state at the time of measurement.

In step S202, the first control circuit 110 causes the imaging unit 170 to start successive imaging. In addition, the first control circuit 110 causes the driving mechanism 160 to move the imaging unit 170 at a predetermined speed and along a predetermined route. At this time, the rough scan movement pattern 520 recorded in the first storage circuit 130 is used.

In step S203, the first control circuit 110 determines whether the imaging by the imaging unit 170 or the movement by the driving mechanism 160 is not performed normally, or whether the imaging should be retried from the start due to failure, etc. If the imaging or movement is not performed normally or if the imaging should be retried from the start, the processing advances to step S204.

In step S204, the first control circuit 110 warns the user, indicating that the imaging or movement is not performed normally or that the imaging should be retried from the start. Subsequently, the processing returns to step S201.

If the determination in step S203 shows that the imaging or movement is performed normally and the imaging need not be retried, the processing advances to step S205.

In step S205, the first control circuit 110 determines whether or not the rough scan should be ended. For example, if the predetermined scan has been completed, the first control circuit 110 determines that the processing should be ended. If it is determined that the processing should not be ended, the processing advances to step S206.

In step S206, the first control circuit 110 refers to the X to Y direction change condition 526 and determines whether or not the moving direction should be changed from the X-axis direction to the Y-axis direction. Unless the moving direction is changed, the processing advances to step S208. If the moving direction is to be changed, the processing advances to step S207.

In step S207, the first control circuit 110 causes the driving mechanism 160 to change the moving direction of the imaging unit 170. Subsequently, the processing advances to step S208.

In step S208, the first control circuit 110 refers to the Y to X direction change condition 527 and determines whether or not the moving direction should be changed from the Y-axis direction to the X-axis direction. Unless the moving direction is changed, the processing returns to step S203. If the moving direction is to be changed, the processing advances to step S209.

In step S209, the first control circuit 110 causes the driving mechanism 160 to change the moving direction of the imaging unit 170. Subsequently, the processing returns to step S203.

If it is determined in step S205 that the rough scan should be ended, the processing advances to step S210.

In step S210, the first control circuit 110 causes the imaging unit 170 to end successive imaging. In addition, the first control circuit 110 causes the driving mechanism 160 to stop moving the imaging unit 170.

In step S211, the first control circuit 110 processes the data obtained by the successive imaging. Based on the analysis of the obtained data, the first control circuit 110 determines the position of the sample 300, the positions of the cells 324 in the sample 300, and the number of cells 324 included in the sample 300. In addition, the first control circuit 110 prepares data suitable for the transmission to the controller 200. The image data obtained by the successive imaging may be video data or data representing a plurality of still images. If the position of the sample 300, the positions of the cells 324 in the sample 300, and the number of cells 324 included in the sample 300 are to be analyzed by the controller 200, the first control circuit 110 does not have to analyze these.

In step S212, the first control circuit 110 transmits the images and analysis results obtained by the successive imaging by the imaging unit 170 to the controller 200. The images may be transmitted in step S212 at a time; alternatively, they may be transmitted at proper times in the repetition processing from step S203 to step S209. The rough scan is completed as above, and the processing returns to the observation apparatus control processing.

Turning back to FIG. 4, the remaining processing of the observation apparatus control will be described. After the rough scan processing in step S107, the processing advances to step S108. In step S108, the first control circuit 110 determines whether or not manual position designation is performed. To be specific, it is determined whether an imaging instruction is received, with the imaging position designated by the controller 200. For example, the user can designate a position based on the image of the entire sample 300 obtained by the rough scan processing. The user can designate a position based on an image obtained in previous imaging, in place of the images obtained by the rough scan processing. Unless an imaging instruction is received, the processing advances to step S110. If an imaging instruction is received, the processing advances to step S109.

In step S109, the first control circuit 110 causes the driving mechanism 160 to move the imaging unit 170 to a designated position and causes the imaging unit 170 to acquire an image at that position. The first control circuit 110 transmits the acquired image to the controller 200 by way of the first communication device 192. Subsequently, the processing advances to step S110.

In step S110, the first control circuit 110 determines whether or not the current time is a time when the measurement should be started. Unless the current time is a measurement start time, the processing advances to step S112. If the current time is a measurement start time, the processing advances to step S111. The measurement start time may be predetermined, for example, at the intervals of one hour. The measurement start time need not be dependent on time; it may be determined in accordance with the state of cells 324 or medium 322. In the present embodiment, measurement is repeatedly performed whenever the measurement start time comes. Therefore, an identical imaging position may be imaged a larger number of times in the second mode (measurement) than in the first mode (rough scan).

In step S111, the first control circuit 110 performs measurement processing. In other words, the first control circuit 110 causes the imaging unit 170 to repeatedly take an image, while simultaneously causing the driving mechanism 160 to move the imaging unit 170. The first control circuit 110 performs predetermined processing for an image taken by the imaging unit 170 and records a requested result in the first storage circuit 130. Subsequently, the processing advances to step S112.

Figure 9:
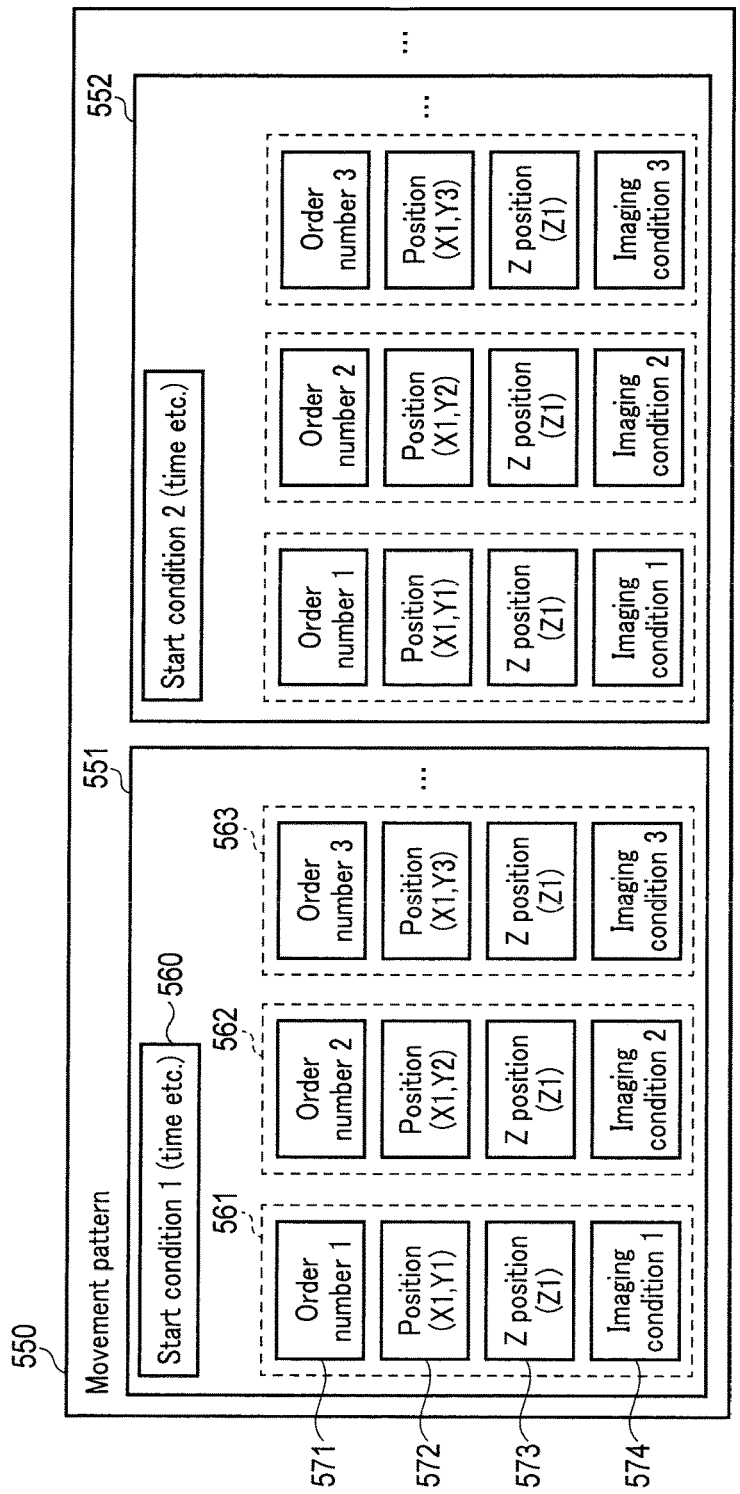
FIG. 9 is an explanatory diagram illustrating a movement pattern used by an observation apparatus according to one embodiment.

The movement pattern according to which the driving mechanism 160 moves the imaging unit 170 in the measurement processing will be described with reference to FIG. 9. FIG. 9 shows an example of the movement pattern 550. The movement pattern 550 such as that shown in FIG. 9 is recorded in the first storage circuit 130. The movement pattern 550 is determined, for example, based on the analysis results of image data obtained by the rough scan processing. This analysis made be performed by the first control circuit 110 according to a predetermined rule or by the second control circuit 210 according to a predetermined rule. Alternatively, the analysis may be performed by the user.

The range in which an image is taken by the measurement processing determined by the movement pattern 550 is, for example, the following range. For example, the range imaged by the measurement processing is a range in which the sample 300 is specified as being arranged, based on the image data obtained by the rough scan processing. Alternatively, the range imaged by the measurement processing is a range in which cells of interest, such as a cell colony, are specified as being located, at the start of measurement. Alternatively, the range imaged by the measurement processing is a range in which the occurrence of a noteworthy change is indicated by the imaging performed a number of times. In addition, a focus position of each of the imaging positions for the measurement processing may be determined based on the image data obtained by the rough scan processing.

The first control circuit 110 controls the driving mechanism 160 and the imaging unit 170 in accordance with the movement pattern 550. In other words, the movement pattern 550 includes operation procedures of the driving mechanism 160 and the imaging unit 170. As shown in FIG. 9, the movement pattern 550 includes a first movement pattern 551 indicative of a first-time movement pattern, a second movement pattern 552 indicative of a second-time movement pattern, etc. The first movement pattern 551 and the second movement pattern 552 may be the same or different. The number of data of movement patterns increases or decreases in accordance with the number of times measurement is performed. If measurement is performed using the same movement pattern, only one movement pattern is prepared.

The first movement pattern 551 will be described by way of example. The first movement pattern 551 includes the following information. That is, the first movement pattern 551 includes a start condition 560. This start condition 560 includes a condition under which the measurement start is determined in step S110.

In the first movement pattern 551, first imaging information 561, second imaging information 562, third imaging information 563, etc. are recorded. The first imaging information 561 will be described by way of example. The first imaging information 561 includes an order 571, a position 572, a Z position 573 and an imaging condition 574. The order 571 is indicated by serial numbers which are assigned to the image operations performed for respective positions. The position 572 includes an X coordinate and a Y coordinate of an imaging position. The X coordinate and the Y coordinate are values used by the position control unit 111 for the control of the driving mechanism 160. The Z position 573 includes a Z coordinate of an imaging position. The Z coordinate is a value used by the imaging control unit 112 for the control of the imaging optical system 172. The imaging condition 574 includes exposure conditions, such as a shutter speed and an aperture value, and other imaging conditions. The imaging conditions may differ, depending upon each imaging operation, they may be the same for the imaging operations included in the first movement pattern 551, or they may be the same for all imaging operations included in the movement pattern 550. Likewise, each of the second imaging information 562 and the third imaging information 563 includes information regarding an order, a position, a Z position and an imaging condition. Where an imaging plane is fixed and is not moved in the Z direction, the information on the Z position 573 may be omitted. Where the imaging condition is fixed and is not changed, the information on the imaging condition 574 may be omitted.

In the above description, a video is taken in the rough scan processing, but this is not restrictive. In the rough scan processing, still images may be taken for the respective position coordinates of the imaging unit 170, and analysis may be performed based on the still images. A video may be taken in the measurement processing as well.

The image acquisition performed in measurement processing will be described, referring to the schematic diagram shown in FIG. 10. The observation apparatus 100 repeatedly takes an image, while changing its position in the X direction and Y direction, for example, in the first plane, and a plurality of images are acquired thereby. The image processing circuit 140 synthesizes these images, thereby preparing one first image 611 of the first plane. The first plane is a plane perpendicular to the optical axis of the imaging unit 170, i.e., a plane parallel to the transparent plate 102. Further, the observation apparatus 100 changes the imaging position in the thickness direction to a second plane and to a third plane, and repeatedly takes an image, while changing its position in the X direction and Y direction in each of the planes, and a second image 612 and a third image 613 are acquired thereby. The thickness direction is a Z-axis direction, namely, the optical axis direction of the imaging unit 170, and is perpendicular to the transparent plate 102. In this manner, an image at each three-dimensional position is acquired. In the above, a description was given of an example in which an image is repeatedly taken, with the imaging plane being changed in the Z direction. Instead of this, an image may be repeatedly taken, with the imaging plane being changed only in the X direction and Y direction (not in the Z direction). In this case, a synthesis image of one plane is obtained. In the method for acquiring the first image 611, the second image 612 and third image 613, a scan may be performed in the X direction and Y direction, with the position in the Z-axis direction being kept fixed, and after the position is changed in the Z-axis direction, a scan may be performed in the X direction and Y direction.

Alternatively, an image of a given position in the X direction and Y direction may be taken a number of times, with the position being changed in the Z-axis direction, and this operation may be performed, with the scan position being changed in the X direction and Y direction.

Figure 11:
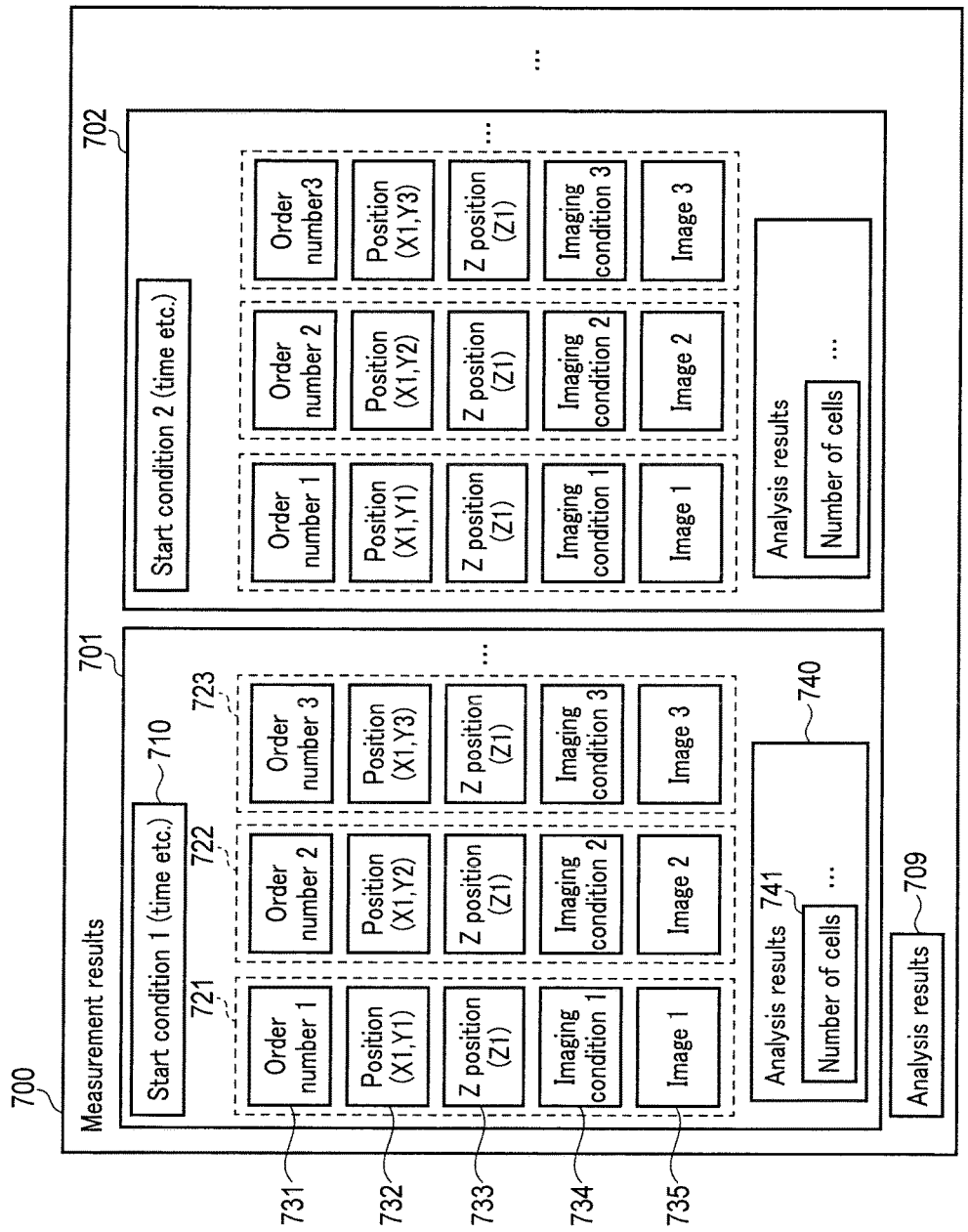
FIG. 11 schematically illustrates an exemplary configuration of data representing measurement results obtained by a measurement system according to one embodiment.

An example of a data structure of measurement results obtained as above and recorded in the first storage circuit 130 is shown in FIG. 11. As shown in FIG. 11, the measurement results 700 include first data 701 obtained by first-time measurement, second data 702 obtained by second-time measurement, etc. The number of data increases or decreases in accordance with the number of times measurement is performed.

The first data 701 will be described by way of example. The first data 701 includes a start condition 710. This start condition 710 includes a condition under which the measurement start is determined in step S110. For example, a measurement start time is predetermined, and when measurement is started at this measurement start time, the measurement start time is recorded as a start condition 710.

In the first data 701, first image information 721, second image information 722, third image information 723, etc. are recorded. Each of these data is a set of data acquired in one-time imaging. The first image information 721 will be described by way of example. The first image information 721 includes an order 731, a position 732, a Z position 733, an imaging condition 734, and an image 735. The order 731 is indicated by serial numbers which are assigned to the image operations performed for respective positions. The position 732 includes an X coordinate and a Y coordinate of an imaging position. The X coordinate and the Y coordinate are values used in the control of the driving mechanism 160 and are acquired by the position control unit 111, for example. The Z position 733 includes a Z coordinate of an imaging position. The Z coordinate is a value used in the control of the imaging optical system 172 and is acquired by the imaging control unit 112, for example. The imaging condition 734 includes exposure conditions, such as a shutter speed and an aperture value, and other imaging conditions. The imaging conditions may differ, depending upon each imaging operation, they may be the same for the imaging operations included in the first data 701, or they may be the same for all imaging operations included in the measurement results 700. The image 735 is image data obtained by the imaging. Likewise, each of the second image information 722 and the third image information 723 includes information regarding an order, a position, a Z position, an imaging condition and an image. Where an imaging plane is not moved in the Z direction, the information on the Z position may be omitted.

The first data 701 includes analysis results 740. The analysis results 740 include a cell number 741 representing the number of cells or cell groups measured by the image processing circuit 140. The analysis results 740 also include a plane image obtained by synthesizing the images of the same Z position. The analysis results 740 also include a three-dimensional image obtained by synthesizing all images 735. The analysis results 740 may include a depth-synthesis image.

Figure 12:
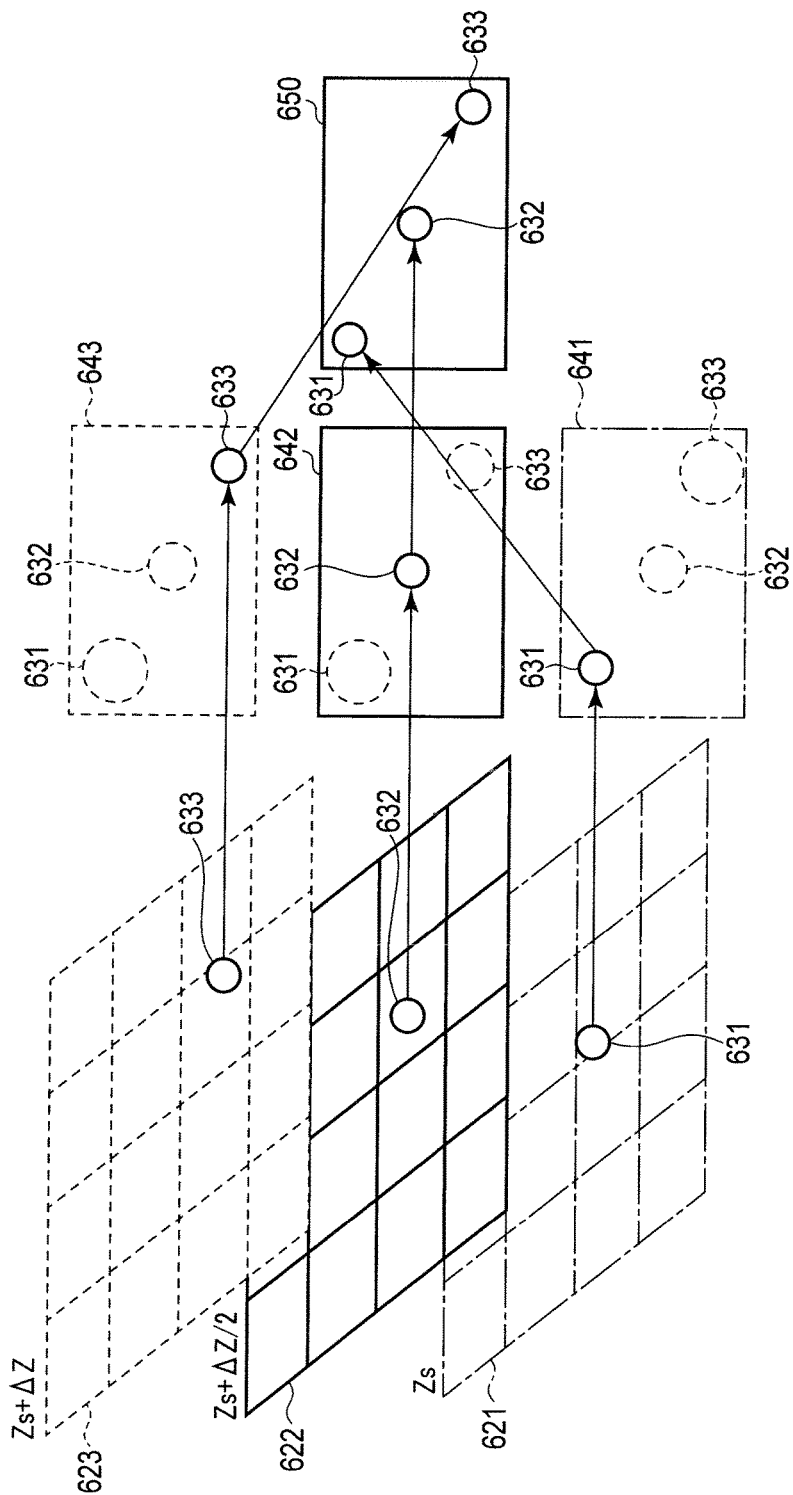
FIG. 12 is an explanatory diagram illustrating depth synthesis performed by an observation apparatus according to one embodiment.

The depth-synthesis image will be described with reference to FIG. 12. Consideration will be given to the case where a first cell 631 is present in the first plane 621 whose Z coordinate is Zs, a second cell 632 is present in the second plane 622 whose Z coordinate is Zs+ΔZ/2, and a third cell 633 is present in the third plane 623 whose Z coordinate is Zs+ΔZ. Let us assume that that the imaging performed with the focus position being changed creates a first image 641 in which the first plane 621 is in focus, a second image 642 in which the second plane 622 is in focus, and a third image 643 in which the third plane 623 is in focus. In the first image 641, the first cell 631 is in focus, and the other cells are not. Likewise, in the second image 642, the second cell 632 is in focus, and the other cells are not. In the third image 643, the third cell 633 is in focus, and the other cells are not. In the depth-synthesis image 650, an image of the first cell 631 included in the first image 641, an image of the second cell 632 included in the second image 642, and an image of the third cell 633 included in the third image 643, are synthesized with one another. As a result, in the resultant depth-synthesis image 650, the first cell 631, the second cell 632 and the third cell 633 are all in focus. Such a depth-synthesis image may be included in the analysis results 740.

Like the first data 701, the second data 702 includes a start condition, first image data, second image data, third image data, analysis results, etc.

As described above, a focus position of the imaging unit is unchanged in the rough scan processing. On the other hand, the focus position of the imaging unit may be changed in the measurement processing.

The measurement results 700 can include analysis results 709 of all measurement that are obtained based on the first data, second data, etc. All measurement results 700 may be recorded in one file; alternatively, part of the measurement results 700 may be recorded in one file.

Turning back to FIG. 4, a description will be continued. In step S112, the first control circuit 110 determines whether or not a request for information is made by the controller 200. For example, the data obtained in step S111 is requested by the controller 200. Unless the request for information is made, the processing advances to step S114. If the request for information is made, the processing advances to step S113.

In step S113, the first control circuit 110 transmits the information requested by the controller 200 to the controller 200 through the first communication device 192. Subsequently, the processing advances to step S114.

In step S114, the first control circuit 110 determines whether or not the observation apparatus control processing should be ended. If it is determined that the observation apparatus control processing should be ended, the observation apparatus control processing is brought to an end. For example, when a series of measurements are ended, and the observation apparatus 100 is removed from the incubator, the observation apparatus control processing is brought to an end. Unless the observation apparatus control processing is brought to an end, the processing advances to step S115.

In step S115, the first control circuit 110 determines whether or not the power source should be turned off. For example, if the standby time, which is from the measurement in step S111 to the next measurement, is long, the first control circuit 110 determines that the power source should be turned off to suppress the power consumption. Unless the power source is turned off, the processing returns to step S104. If it is determined that the power source should be turned off, the processing advances to step S116.

In step S116, the first control circuit 110 turns off each portion of the observation apparatus 100. Subsequently, the processing returns to step S101. In the above manner, the observation apparatus 100 repeatedly performs measurement.

Figure 13B:
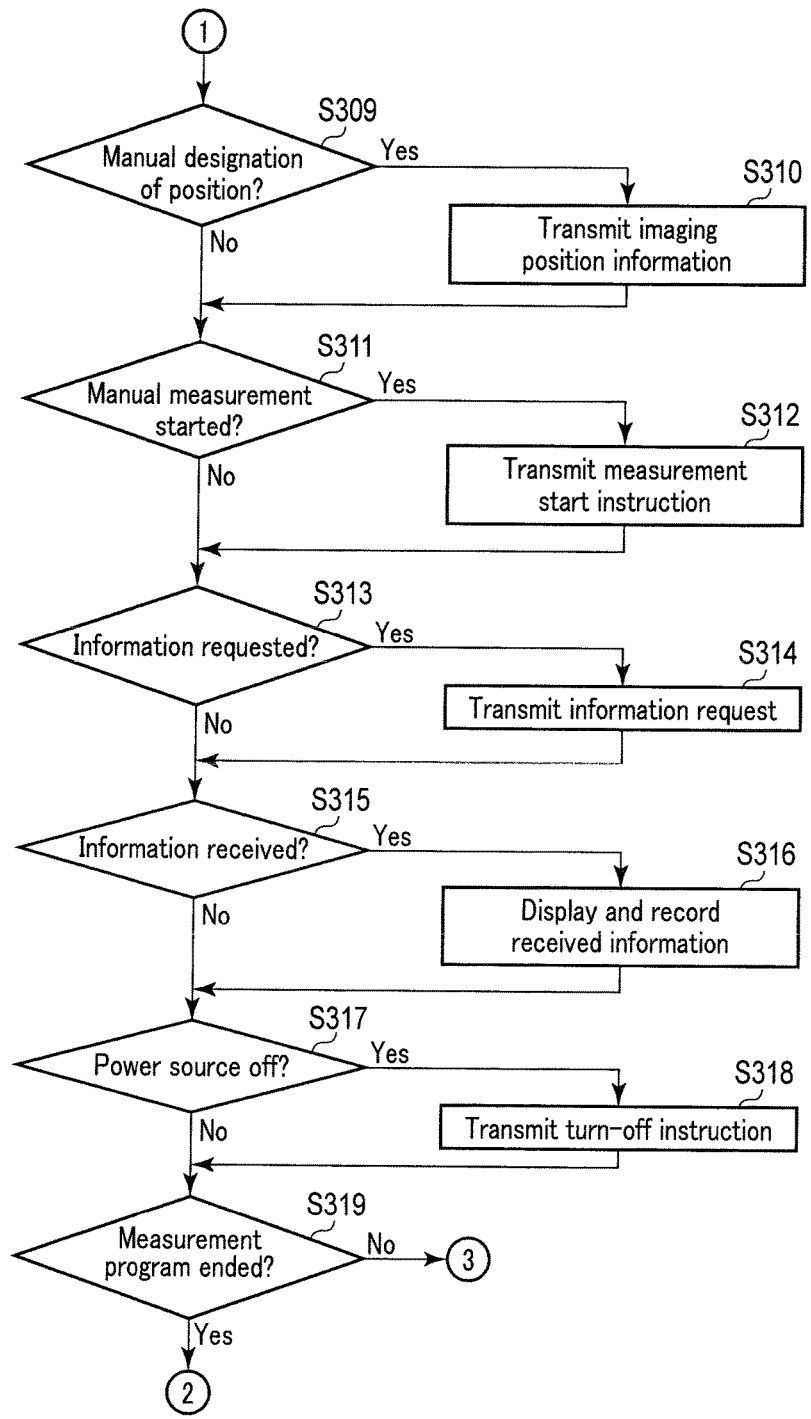
FIG. 13B is a flowchart illustrating an example of processing performed by the controller according to the embodiment.

Next, the operation of the controller 200 will be described with reference to the flowcharts shown in FIGS. 13A and 13B. The processing indicated in the flowcharts of FIGS. 13A and 13B starts when the observation apparatus 100, controller 200 and sample 300 are set in place.

In step S301, the second control circuit 210 determines whether or not a measurement program according to the present embodiment is activated. Unless the measurement program is activated, the processing of step S301 is repeated. The controller 200 is not limited to the functions of the controller of the measurement system of the present embodiment but may have various functions. Therefore, when the measurement program is not activated, the controller 200 may operate as a system other than the measurement system 1. If it is determined that the measurement program is activated, the processing advances to step S302.

In step S302, the second control circuit 210 establishes communications with the observation apparatus 100. This operation is related to step S103 of the observation apparatus control performed by the observation apparatus 100. That is, the observation apparatus 100 and the controller 200 operate such that the communications between them are established. The communications established then may be low-power-consumption communications being irrelevant to step S103 of the observation apparatus control and only enabling the transmission of an instruction to turn on the observation apparatus 100.

In step S303, the second control circuit 210 determines whether or not the user is requesting that the observation apparatus 100 be turned on. For example, if an instruction to turn on the observation apparatus 100 is supplied from the input device 274, the second control circuit 210 determines that the user is requesting that the power source be turned on. Unless the instruction to turn on the observation apparatus 100 is supplied, the processing advances to step S305. If the instruction to turn on the observation apparatus 100 is supplied, the processing advances to step S304. In step S304, the second control circuit 210 transmits an instruction to turn on the observation apparatus 100 to the observation apparatus 100. Subsequently, the processing advances to step S305. This operation is related to step S101 of the observation apparatus control performed by the observation apparatus 100. Upon receipt of the instruction to turn on the observation apparatus 100 from the controller 200, the observation apparatus 100 is turned on in step S102. The communication means used in the embodiment may be low-power-consumption communications such as Bluetooth Low Energy.

In step S305, the second control circuit 210 determines whether or not the user is requesting transmission of information to the observation apparatus 100. For example, if an instruction to transmit information is supplied from the input device 274, the second control circuit 210 determines that the user is requesting transmission of information. The information the transmission of which is requested is information on measurement conditions etc. Unless the transmission of information is requested, the processing advances to step S307. If the transmission of information is requested, the processing advances to step S306. In step S306, the second control circuit 210 transmits the information entered from the input device 274 to the observation apparatus 100. Subsequently, the processing advances to step S307. This operation is related to step S104 of the observation apparatus control performed by the observation apparatus 100. The observation apparatus 100 acquires the information transmitted from the controller 200 to the observation apparatus 100 in step S105.

In step S307, the second control circuit 210 determines whether or not the user is requesting that the observation apparatus 100 perform a rough scan. For example, if an instruction related to the rough scan is supplied from the input device 274, the second control circuit 210 determines that the user is requesting execution of the rough scan. Unless the rough scan is requested, the processing advances to step S309. If the rough scan is requested, the processing advances to step S308. In step S308, the second control circuit 210 transmits an instruction to start the rough scan to the observation apparatus 100. Subsequently, the processing advances to step S309. This operation is related to step S106 of the observation apparatus control performed by the observation apparatus 100. The observation apparatus 100 performs rough scan processing in step S107, based on the rough scan start instruction transmitted from the controller 200 to the observation apparatus 100.

In step S309, the second control circuit 210 determines whether or not the user manually designates a position to be imaged by the observation apparatus 100. For example, if an imaging position is entered from the input device 274, the second control circuit 210 determines that imaging position has been designated. Unless the imaging position is designated, the processing advances to step S311. If the imaging position is designated, the processing advances to step S310. In step S310, the second control circuit 210 transmits the imaging position entered from the input device 274 to the observation apparatus 100. Subsequently, the processing advances to step S311. This operation is related to step S108 of the observation apparatus control performed by the observation apparatus 100. Position adjustment is made in step S109 in accordance with the imaging position transmitted from the controller 200 to the observation apparatus 100. An image is acquired at that position and transmitted.

In step S311, the second control circuit 210 determines whether or not the user is requesting that the observation apparatus 100 start measurement. For example, if an instruction to start measurement by the observation is supplied from the input device 274, the second control circuit 210 determines that the user is requesting start of measurement. If the start of measurement is not requested, the processing advances to step S313. If the start of measurement is requested, the processing advances to step S312. In step S312, the second control circuit 210 transmits an instruction to start measurement to the observation apparatus 100. Subsequently, the processing advances to step S313. This operation is related to step S110 of the observation apparatus control performed by the observation apparatus 100. Measurement is performed in step S111 in accordance with the instruction transmitted from the controller 200 to the observation apparatus 100.

In step S313, the second control circuit 210 determines whether or not the user is requesting acquiring information from the observation apparatus 100. For example, if an instruction to request information is supplied from the input device 274, the second control circuit 210 determines that the user is requesting information. The information requested then is, for example, information on the sample 300 obtained by the observation apparatus 100. The information can be information contained in the measurement results 700 described with reference to FIG. 11, including image data on the sample 300 and the number of cells or cell groups in the sample 300. Unless the information is requested, the processing advances to step S315. If the information is requested, the processing advances to step S314. In step S314, the second control circuit 210 transmits an instruction to transmit the user's requested information to the observation apparatus 100. Subsequently, the processing advances to step S315. This operation is related to step S112 of the observation apparatus control performed by the observation apparatus 100. The information requested in step S113 is transmitted from the observation apparatus 100 to the controller 200 in accordance with the information request transmitted from the controller 200 to the observation apparatus 100.

In step S315, the second control circuit 210 determines whether or not the information requested in step S314 is received. Unless the information is received, the processing advances to step S317. If the information is received, the processing advances to step S316. In step S316, the second control circuit 210 displays the received information on the display device 272 or records it in the second storage circuit 230. Subsequently, the processing advances to step S317.

In step S317, the second control circuit 210 determines whether or not the user is requesting that the observation apparatus 100 be turned off. For example, if an instruction to turn off the observation apparatus 100 is supplied from the input device 274, the second control circuit 210 determines that the user is requesting that the power source be turned off. Unless the instruction to turn off the observation apparatus 100 is supplied, the processing advances to step S319. If the instruction to turn off the observation apparatus 100 is supplied, the processing advances to step S318. In step S318, the second control circuit 210 transmits an instruction to turn off the observation apparatus 100 to the observation apparatus 100. Subsequently, the processing advances to step S319. This operation is related to step S115 of the observation apparatus control performed by the observation apparatus 100. The observation apparatus 100 is turned off in step S116 in accordance with the turn-off instruction transmitted from the controller 200 to the observation apparatus 100.

In step S319, the second control circuit 210 determines whether or not the measurement program comes to an end. If the measurement program ends, the processing returns to step S301. Unless the measurement program ends, the processing returns to step S303. As can be seen from this, the above operation is repeatedly executed.

As described above, the measurement by the measurement system 1 is repeatedly performed at predetermined timings and under predetermined conditions. Measurement timings and measurement conditions may be entered by the user from the controller 200 and set in the observation apparatus 100. The measurement by the measurement system 1 may be manually performed based on a user's instruction when the instruction to start the measurement is entered by the user from the controller 200 and is supplied to the observation apparatus 100.

<Advantage of the Measurement System>

The measurement system 1 of the present embodiment can take an image of cells existing in a wide range in the state where the sample 300 is statically placed in the incubator. It should be noted that an image can be repeatedly taken with time. The user can therefore observe how the cells change with time and analyze the change. According to the present embodiment, a rough scan is performed. This rough scan enables quick understanding of an overview of the sample 300. In addition, information can be acquired from the images obtained in the rough scan, as to which image portion should be focused on in the subsequent measurement. A movement pattern 550 can be determined based on this information. The imaging conditions in the measurement are based on the movement pattern 550 determined based on the rough scan.

<Modifications>

In connection with the above embodiment, reference was made to the case where the observation apparatus 100 processes the images obtained by the imaging unit 170 and analyses the measurement results. However, this is not restrictive. The second control circuit 210 of the controller 200 may perform at least one of these processes if unprocessed data is transmitted from the observation apparatus 100 to the controller 200. In other words, an apparatus, one aspect of the present invention, can be modified in a number of ways. For example, it may be designed to cooperate with a number of apparatuses to attain the above-mentioned functions. An observation method, another aspect of the present invention, comprises: causing an imaging unit to take an image of a target object; moving the imaging unit to change an observation position of the target object; and controlling the imaging unit while switching between (i) a first mode in which the imaging unit takes successive images while simultaneously being moved at a high speed, and (ii) a second mode in which the imaging unit successively takes higher resolution images than those of the first mode while simultaneously being moved at a speed lower than that of the first mode. The target object need not be a cell but may be a sheet-like material, the surface of a material or the like. The target object may be anything other than those mentioned in the embodiment as long as the relative positional relationship between the target object and the imaging unit changes. Instead of the structure wherein the target object is fixed and the driving mechanism is provided for the imaging unit, the driving mechanism may be provided for the target object. The above-mentioned advantages and object can be attained provided that the relative position between the imaging unit and the target object changes.

In the above-mentioned embodiment, reference was made to the case where the transparent plate 102 covers the top of the casing 101 of the observation apparatus 100, and the sample 300 is placed on top of the casing 101. However, this is not restrictive. Depending upon the size of the target object and the shape of the casing, the transparent plate 102 need not be employed. In this case, the casing is just a hollow member. The shape of the observation apparatus 100 may be properly varied in accordance with the morphology of the sample 300, the observation direction, or the like.

The imaging unit 170 may be a twin-lens unit comprising a first imaging optical system, a first image sensor, a second imaging optical system and a second image sensor. The first imaging optical system and the first image sensor may be used for a rough scan, while the second imaging optical system and the second image sensor may be used for measurement. For example, the first image sensor may be a monochrome sensor, and the second image sensor may be a color sensor. The second image sensor may not be a color sensor but a monochrome sensor suitable for measurement, e.g., a monochrome sensor having a larger number of pixels than the first image sensor. Alternatively, the second image sensor may be an infrared (IR) sensor. Both of the two image sensors may be used for measurement. For example, the images obtained by the two image sensors may be synthesized together to obtain high-resolution images. In the measurement, the second image sensor may take still images, while the first image sensor may take videos.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An observation apparatus comprising:
    an imaging unit which takes images of a target object;
    a driving mechanism which moves the imaging unit to change an observation position of the target object; and
    a control unit which controls the driving mechanism and the imaging unit while switching between (i) a first mode in which the imaging unit takes images while simultaneously being moved at a high speed by the driving mechanism, and (ii) a second mode in which the imaging unit takes images having a higher resolution than that of the images taken in the first mode while simultaneously being moved at a speed lower than that of the first mode.

2. The observation apparatus according to claim 1, wherein an identical observation position is imaged a larger number of times in the second mode than in the first mode.

3. The observation apparatus according to claim 1, wherein
    the imaging unit includes an image sensor which comprises a plurality of pixels and outputs an image signal,
    the imaging unit thins signals of part of the pixels and outputs a resultant image signal in the first mode, and
    an image taken in the second mode has a higher resolution than that of an image taken in the first mode.

4. The observation apparatus according to claim 1, wherein
    the imaging unit includes an image sensor which comprises a plurality of pixels and outputs an image signal,
    the imaging unit adds signals of part of the pixels and signals of remaining part of the pixels to each other and outputs a resultant image signal in the first mode, and
    an image taken in the second mode has a higher resolution than that of an image taken in the first mode.

5. The observation apparatus according to claim 1, wherein the control unit controls the imaging unit such that an image sensor has a higher sensitivity in the first mode than in the second mode.

6. The observation apparatus according to claim 1, wherein
    in the first mode, the control unit keeps a focus position of the imaging unit unchanged, and
    in the second mode, the control unit either changes the focus position of the imaging unit or keeps the focus position unchanged.

7. The observation apparatus according to claim 6, wherein the control unit determines a focus position of each of observation positions for observation in the second mode, based on imaging results obtained in the first mode, and causes the imaging unit to take an image in the second mode, using the determined focus position.

8. The observation apparatus according to claim 1, wherein the control unit controls the imaging unit such that an imaging optical system has a shorter focal distance in the first mode than in the second mode.

9. The observation apparatus according to claim 1, wherein the control unit controls the imaging unit such that an imaging optical system has a smaller opening size of an aperture in the first mode than in the second mode.

10. The observation apparatus according to claim 1, wherein the imaging unit comprises two image sensors having different characteristics.

11. The observation apparatus according to claim 10, wherein the characteristics include at least one of a spectral sensitivity characteristic and a number of pixels.

12. The observation apparatus according to claim 1, wherein the control unit controls the driving mechanism and the imaging unit, based on operation procedures which are determined in accordance with imaging results obtained in the first mode and which indicate how the driving mechanism and the imaging unit operate in the second mode.

13. The observation apparatus according to claim 12, wherein the control unit determines that a region imaged in the second mode based on the imaging results is at least one of a region in which a sample is present, a region in which a cell of interest is present, and a region in which a cell of interest undergoes changing.

14. The observation apparatus according to claim 1, further comprising:
    a communication device for communicating with an external apparatus,
    wherein the control unit performs at least one of (i) controlling an operation of the driving mechanism, (ii) controlling an operation of the imaging unit, (iii) image processing for an image which the imaging unit produces as an imaging result, (iv) transmission of the observation position to the external apparatus, and (v) transmission of information representing an image which the imaging unit produces as an imaging result, based on a signal received from the external apparatus.

15. A measurement system comprising:
an observation apparatus of claim 1 which further comprises a communication device; and
a controller which communicates with the observation apparatus via the communication device and controls the observation apparatus.

16. An observation method comprising:
causing an imaging unit to image a target object;
moving the imaging unit to change an observation position of the target object; and
controlling the imaging unit while switching between (i) a first mode in which the imaging unit takes successive images while simultaneously being moved at a high speed by the driving mechanism, and (ii) a second mode in which the imaging unit takes successive images having a high resolution than that of the images taken in the first mode while simultaneously being moved at a speed lower than that of the first mode.

* * * * *